United States Patent [19]
Bandman et al.

[11] Patent Number: 6,162,431
[45] Date of Patent: Dec. 19, 2000

[54] SERINE/THREONINE PROTEIN KINASE

[75] Inventors: Olga Bandman, Mountain View; Karl J. Guegler, Menlo Park; Preeti Lal, Sunnyvale, all of Calif.

[73] Assignee: Incyte Genomics, Inc., Palo Alto, Calif.

[21] Appl. No.: 09/334,775

[22] Filed: Jun. 16, 1999

Related U.S. Application Data

[62] Division of application No. 08/818,024, Mar. 14, 1997, Pat. No. 5,965,365.

[51] Int. Cl.$^7$ .................................................. A61K 38/51
[52] U.S. Cl. ......................... 424/94.5; 435/183; 435/194
[58] Field of Search ..................................... 435/183, 194

[56] References Cited

PUBLICATIONS

Hardie, G. et al., "The Eukaryotic Protein Kinase Superfamily" *The Protein Kinase Facts Book* (1995) vol. I:7–20.

Isselbacher, K.J. et al. (1994) *Harrison's Principles of Internal Medicine*, pp. 416–431 and 1887.

Egan, S.E., et al., "The pathway to signal achievement" *Nature*, (1993) 365:781–783.

Baynes, C. (GI 1246456), GenBank Sequence Database (Accession Z70308), National Center for Biotechnology Information, National Library of Medicine, Bethesda, Maryland, 20894. (GI 1246460).

Tejedor, F. et al., "minibrian: A New Protein Kinase Family Involved in Postembryonic Neurogenesis in Drosophila" *Neuron* (1995) 14:287–301. (GI 757822 and GI 757823).

Becker, W. et al. (GI 1669684), GenBank Sequence Database (Accession Y09305), National Center for Biotechnology Information, National Library of Medicine, Bethesda, Maryland, 20894. (GI 1669685).

Kentrup, H., et al., "Dyrk, a Dual Specificity Protein Kinase with unique Structural Features Whose Activity is Dependent on Tyrosine Residues Between Subdomains VII and VIII," *The Journal of Biol. Chem.*, 271 (7) :3488–3495 (1996), XP–002069625.

Song, W., et al., Isolation of Human and Murine Homologues of the Drosophila Minibrain Gene: Human Homologue Maps to 21q22.2 in the Down Syndrome "Critical Region", XP–002069626.

TRHUM EMBL Database Entry Q92631, Accession No. Q92631; Feb. 1, 1997, Becker, W., et al., "Protein Kinase (fragment) DYRK4," XP002069627.

EMHUM1 EMBL Database entry HSDYRK4, Acession No. Y09305; Nov. 14, 1996, Becker, W., et al., "H. sapiens mRNA for protein kinase, Dyrk4, partial," XP002069628.

EMEST EMBL Database entry HSAA83586, Accession No. AA083586; Dec. 11, 1996, Hillier et al., "Homo sapiens cDNA clone 549128 5' similiar to WP:F49E11.1 CE05897 serine/threonine protein kinase," XP002069629.

EMEST EMBL Database entry HS11443129, Accession No. AA223535; Feb. 22, 1997, Hillier et al., "Homo sapiens cDNA clone 650804 5' similar to SW:KA23 SCHP0 Q09690 probable serine/threonine–protein," XP002069630.

EMEST EMBL Database entry HS116362, Accession No. W78116; Jun. 25, 1996, Hillier et al., "Soares fetal heart NbHH19W Homo sapiens cDNA clone 346879 3'", XP002069631.

EMEST EMBL Database entry HSAA83468, Accession No. AA083468; Dec. 11, 1996, Hillier et al., "Homo sapiens cDNA clone 549128 3'", XP002069632.

*Primary Examiner*—Karen Cochrane Carlson
*Attorney, Agent, or Firm*—Incyte Genomics, Inc.

[57] ABSTRACT

The present invention provides a human growth factor receptor binding protein (HSTPK) and polynucleotides which encode HSTPK. The invention also provides expression vectors, host cells, agonists, antisense molecules, antibodies, or antagonists. The invention also provides methods for producing HSTPK and for treating disorders associated with expression of HSTPK.

5 Claims, 10 Drawing Sheets

```
                                                         9                  18               27              36              45              54
                                                       NGT  CCT  TTG  GGA  CAG  GTG  GCC  AAG  TGC  TTG  GAT  CAC  AAA  AAC  AAT  GAG  CTG  GTG 63                 72               81              90              99              108
                                                       GCC  CTG  AAA  ATC  ATC  AGG  AAC  AAG  AGG  TTT  CAC  CAG  CAG  GCC  CTG  ATG  GAG
                                                                                                                                         M    E 117                126              135             144             153             162
                                                       CTG  AAG  ATC  CTG  GAA  GCT  CTC  AGA  AAG  AAG  GAC  AAA  GAC  AAC  ACC  TAC  AAT  GTG
                                                        L    K    I    L    E    A    L    R    K    K    D    K    D    N    T    Y    N    V 171                180              189             198             207             216
                                                       GTG  CAT  ATG  AAG  GAC  TTT  TTC  TAC  TTT  CGC  AAT  CAC  TTC  TGC  ATC  ACC  TNN  GAG
                                                        V    H    M    K    D    F    F    Y    F    R    N    H    F    C    I    T    X    E 225                234              243             252             261             270
                                                       CTC  CTG  GGA  ATC  AAC  TTG  TTT  GAG  ATG  AAG  AAT  AAC  AAC  TTT  CAA  GGC  TTC
                                                        L    L    G    I    N    L    F    E    M    K    N    N    N    F    Q    G    F 279                288              297             306             315             324
                                                       AGT  CTG  TCC  ATA  GTT  CGG  GGC  TTC  ACT  CTC  TCT  GNN  NGG  GGG  TGC  TTG  CAG  ATG
                                                        S    L    S    I    V    R    G    F    T    L    S    X    X    X    G    C    L    Q    M 333                342              351             360             369             378
                                                       CTT  TCG  GTA  GAG  AAA  ATC  ATT  CAC  TGT  GAT  CTC  AAG  CCC  GAA  AAT  ATA  GTG  CTA
                                                        L    S    V    E    K    I    I    H    C    D    L    K    P    E    N    I    V    L
```

FIGURE 1A

```
       387         396         405         414         423         432
TAC CAA AAG GGC CAC GCC TCT GTT AAA GTC ANT GAC TTT GGA TCA AGC TGT TAT
 Y   Q   K   G   H   A   S   V   K   V   X   D   F   G   S   S   C   Y 441         450         459         468         477         486
GAA CAC CAG AAA GTA TAC ACG TAC ATC CAA AGC CGG TTC TAC CGA TCC CCA GAA
 E   H   Q   K   V   Y   T   Y   I   Q   S   R   F   Y   R   S   P   E 495         504         513         522         531         540
GTA ATC CTG GGC CAC CCA CAC CCC TAC GAC GTG GCC ATT GAC ATG TGG AGC CTG
 V   I   L   G   H   P   H   P   Y   D   V   A   I   D   M   W   S   L 549         558         567         576         585         594
GGC TGC ATC ACG GCG GAG TTG TAC ACG GGC TAC CCC CTG TTC CCC GGG GAG AAT
 G   C   I   T   A   E   L   Y   T   G   Y   P   L   F   P   G   E   N 603         612         621         630         639         648
GAG GTG GAG CAG CTG GCC TGC ATC ATG GAG GTG CTG GGT CTG CCA CCA GCC GGC
 E   V   E   Q   L   A   C   I   M   E   V   L   G   L   P   P   A   G 657         666         675         684         693         702
TTC ATT CAG ACA GCC TCC AGG AGA CAG ACA TTC TTT GAT TCC AAA GGT TTT CCT
 F   I   Q   T   A   S   R   R   Q   T   F   F   D   S   K   G   F   P 711         720         729         738         747         756
AAA AAT ATA ACC AAC AAC AGG GGG AAA AAA AGA TAC CCA GAT TCC AAG GAC CTC
 K   N   I   T   N   N   R   G   K   K   R   Y   P   D   S   K   D   L
```

FIGURE 1B

```
      765              774              783              792              801              810
ACG ATG GTG CTG AAA ACC TAT GAC ACC AGC TTC CTG GAC TTT CTC AGA AGG TGT
 T   M   V   L   K   T   Y   D   T   S   F   L   D   F   L   R   R   C 819              828              837              846              855              864
TTG GTA TGG GAA CCT TCT CTT CGC ATG ACC CCG GAC CAG GCC CTC AAG CAT GCT
 L   V   W   E   P   S   L   R   M   T   P   D   Q   A   L   K   H   A 873              882              891              900              909              918
TGG ATT CAT CAG TCT CGG AAC CTC AAG CCA CAG CCC AGG CCC CAG ACC CTG AGG
 W   I   H   Q   S   R   N   L   K   P   Q   P   R   P   Q   T   L   R 927              936              945              954              963              972
AAA TCC AAT TCC TTT TTC CCC TCT GAG ACA AGG AAG GAC AAG GTT CAA GGC TGT
 K   S   N   S   F   F   P   S   E   T   R   K   D   K   V   Q   G   C 981              990              999              1008             1017             1026
CAT CAC TCG AGC AGA AAA GCA GAT GAG ATC ACC AAA GAG ACT ACA GAG AAA ACA
 H   H   S   S   R   K   A   D   E   I   T   K   E   T   T   E   K   T 1035             1044             1053             1062             1071             1080
AAA GAT AGC CCC ACG AAG CAT GTT CAG CAT TCA GGT GAT CAG CAG GAC TGT CTC
 K   D   S   P   T   K   H   V   Q   H   S   G   D   Q   Q   D   C   L 1089             1098             1107             1116             1125             1134
CAG CAC GGA GCT GAC ACT GTT CAG CTG CCT CAA CTG GTA GAC GCT CCC AAG AAG
 Q   H   G   A   D   T   V   Q   L   P   Q   L   V   D   A   P   K   K
```

FIGURE 1C

```
      1143              1152              1161              1170              1179              1188
TCA GAG GCA GCT GTC GGG GCG GAG GTG TCC ATG ACC TCC CCA GGA CAG AGC AAA
 S   E   A   A   V   G   A   E   V   S   M   T   S   P   G   Q   S   K 1197              1206              1215              1224              1233              1242
AAC TTC TCC CTC AAG AAC ACA AAC GTT TTA CCC CCT ATT GTA TGA CCT TTG CTG
 N   F   S   L   K   N   T   N   V   L   P   P   I   V 1251              1260              1269              1278              1287              1296
AGG GTA TGT CCT GCT CCT TTC CAC CAG TGA TTT GTA TTA AGA CAG CAC TTA TAT 1305              1314              1323              1332              1341              1350
TGT ACA ATA CTT CAG ACT GTT TTT TTT AAA TAC ATA AAA CTT TAT GTT AAA AAA 1359              1368              1377              1386              1395              1404
CTC TAT TAA CAT GGC CAA TTG GCA TGA CTC CTC TTA TGA GGG ATG GGG GAG GAT 1413              1422              1431              1440              1449              1458
GTC CTT GCA CTT AAA CTC ATT CCA TAT GCA TCT GTG TGT GTA GAG GGG GCG GGT 1467              1476              1485              1494
AGT TTT GAA CTC TCA GTG TTA CAG CAT CAT TAA TGG AAC TC
```

FIGURE 1D

```
1   M E L - - - - - - - - - - - - - - - - - - - - - - - - - - -                                HPSTK
1   M T L F E P S T S G N R M G Y R G S S N S S S G V G S G G S            g1246460
1   M H - - - - - - - - - - - - - - H H S S P S S S S E V - - -            g757823
1   - - - - - - - - - - - - - - - - - - - - - - - - - - - - -              g1669685

4   - - - - - - - - - - - - - - - - - - - - - - - - - - - - -              HPSTK
31  G S L M T Q S I G G P N K H L S A S H S T L N T A S T H D M            g1246460
14  - R A M Q A R I - - P N H F R E P A S G P L R K L S V D L I            g757823
1   - - - - - - - - - - - - - - - - - - - - - - - - - - - - -              g1669685

4   - - - - - - - - - - - - - - - - - - - - - - - - - - - - -              HPSTK
61  M H S K I P K S P S N E S L S R S H T S S S G G S Q G G H N            g1246460
41  K T Y K H I N E V Y Y A K K R R A Q Q T Q G D D D S S N K -            g757823
1   - - - - - - - - - - - - - - - - - - - - - - - - - - - - -              g1669685

4   - - - - - - - - - - - - - - - - - - - - - - - - - - - - -              HPSTK
91  S N S G S N S G F R P E D A V Q T F G A K L V P F F E K N E I          g1246460
71  K E - - - - - - - - - - - - - - - - - - - - - - - - - - -              g757823
1   - - - - - - - - - - - - - - - - - - - - - - - - - - - - -              g1669685

4   - - - - - - - - - - - - - - - - - - - - - - - - - - - - -              HPSTK
121 Y N Y T R V F F V G S H A K K Q A G V I G G A N N G G Y D D            g1246460
73  - - R K L Y - - - - - - - - - - - - - - - - N D G Y D D -              g757823
1   - - - - - - - - - - - - - - - - - - - - - - - - - - - - -              g1669685
```

FIGURE 2A

```
  4    - - - - - - - - - - - - - - - - - - - - - - - - - - - - - - - - - - -    HPSTK
151    E N G S Y Q L V V H D H I A Y R Y E V L K V I G K G S F G Q               g1246460
 83    D N H D Y I I K N G E K F L D R Y E I D S L I G K G S F G Q               g757823
  1    - - - - - - - - - - - - - - - - - - - - - - - - - - - - - - - - - - -    g1669685

4    - - - - - - - - - - - - - - - - - - - - - - - - - - - - - - - - - - -    HPSTK
181    V I K A F D H K Y Q Q Y V A L K L V R N E K R F H R Q A D E               g1246460
113    V V K A Y D H E E Q C H V A I K I I K N K K P F L N Q A Q I               g757823
  1    - - - - - - - - - - - - - - - - - - - - - - - - - - - - - - - - - - -    g1669685

4    - - K I L E A L R K K D K D N T Y N V V H M K D F F Y F R N               HPSTK
211    E I R I L D H L R R Q D S D G T H N I I H M L D Y F N F R N               g1246460
143    E V K L L E M M N R A D A E N K Y Y I V K L K R H F M W R N               g757823
  1    - - - - - - - - - - - - - - - - - - - - - - - - - - - - - - - - - - -    g1669685

32    H F C I T X E L L G I N L F E L M K N N F Q G F S L S I V                 HPSTK
241    H K C I T F E L L S I N L Y E L I K R N K F Q G F S L M L V               g1246460
173    H L C L V F E L L S Y N L Y D L L R N T N F R G V S L N L T               g757823
  1    - - - - - - - - P - - - - - - - - - - - - - - - - - - - - - - - - -    g1669685

62    R G F T L S X X G C L Q M L S V E - - - K I H C D L K P                   HPSTK
271    R K F A Y S M L L C L D L L - - - Q K N R L I H C D L K P                 g1246460
203    R K F A - - Q Q L C T A L F L S T P E L N I H C D L K P                   g757823
  2    - - - - - - Y D - - - - - - - - - - - - - - - - - - -                     g1669685
```

FIGURE 2B

```
 88  E N I V L Y Q K G H A S V K V X D F G S S C Y E H Q K V Y T   HPSTK
297  E N V L L K Q Q G R S G I K V I D F G S S C F D D Q R I Y T   g1246460
231  E N I L L C N P K R S A I K I V D F G S S C Q L G Q R I Y H   g757823
  4  - - - - - - - - - - - - - - - - - - - - - - - V A - - - - -  g1669685

118  Y I Q S R F Y R S P E V I L G H P H P Y D V A I D M W S L G   HPSTK
327  Y I Q S R F Y R A P E V I L G T - - K Y G M P I D M W S L G   g1246460
261  Y I Q S R F Y R S P E V L L G I - - Q Y D L A I D M W S L G   g757823
  6  - - - - - - - - - - - - - - - - - - - - - I D M W S L G      g1669685

148  C I T A E L Y T G Y P L F P G E N E V E Q L A C I M E V L G   HPSTK
355  C I L A E L L T G Y P L L P G E D E N D Q L A L I E L L G     g1246460
289  C I L V E M H T G E P L F S G C N E V D Q M N K I V E V L G   g757823
 13  C I T A E L Y T G Y P L F P G E N E V E Q L A C I M E V L G   g1669685

178  L P P A G F I Q T A S R R Q T F F D S K - G F P K N I T N -   HPSTK
385  M P P P K S L E T A K R A R T F I T S K - G Y P R Y C T A T   g1246460
319  M P P K Y L L D Q A H K T R K F F D K I V A D G S Y V L K K   g757823
 43  L P P A G F I Q T A S R R Q T F F D S K - G F P K N I T N -   g1669685

206  N R G K K R Y - - - - - - - - - - - - - - - - P D S K D       HPSTK
414  S M P D G S V L A G A R S K R G K M - - R G P P A S R S       g1246460
349  N Q N G R K Y K P P G S R K L H D I L G V E T G G P G G R R   g757823
 71  N R G K K R Y - - - - - - - - - - - - - - - - P D S K D       g1669685
```

FIGURE 2C

```
218  L T M V L K T Y D T - - S F L D F L R R C L V W E P S L R M    HPSTK
441  W S T A L K N M G D E L - F V D F L K R C L D W D P E T R M    g1246460
379  L D E P G H S V S D Y L K F K D L I L R M L D F D P K T R V    g757823
83   L T M V L K T Y D T - - S F L D F L R R C L V W E P S L R M    g1669685

246  T P D Q A L K H A W I H Q S R N L K P Q P R P Q T L R K S N    HPSTK
470  T P A Q A L K H H K W L R R - - - - - - - - - - - - - - - -    g1246460
409  T P Y Y A L Q H N F F K R T A D E A T N T S G A G A T A N A    g757823
111  T P D Q A L K H A W I H Q S R N L K P Q P R P Q T L R K S N    g1669685

276  S F F P S E T R K D K V Q G C H H S S R K A D E I T K E T T    HPSTK
483  - - - - - - - - - - - - - - - - - - - - - - - - - - - - -     g1246460
439  G A G G S G S S G A G G S S G G V G G G L G A S N S S S G      g757823
141  S F F P S E T R K D K V Q G C H H S S R K - D E I T K E T T    g1669685

306  E K T K D S P T K H V Q H S G D Q Q D C L Q H G A D T V Q L    HPSTK
483  - - - - - - - - - - - - - - - - - - - - - - - - - - - - -     g1246460
469  A V S S S A A A P T A A T A A A G S S G S G S S V G           g757823
170  E K T K D S P T K H V Q H S G D Q Q D C L Q H G A D T V Q L    g1669685
```

FIGURE 2D

```
336  P Q L V D A P K K S E A A V G A E V S M T S P G Q S K N F S   HPSTK
483  - - - - - - - - - - R L P N P - - - P R D G L E S M G G       g1246460
499  G G S S A A Q Q Q Q A M P L P L P L P P L A G P G G           g757823
200  P Q L V D A P K K S E A A V G A E V S M T S P G Q S K N F S   g1669685

366  L K N T N V L P P I V                                          HPSTK
498  L A D H E V C F I F                                            g1246460
529  A S D G Q C H D D R R                                          g757823
230  L K N T N V L P P I V                                          g1669685
```

FIGURE 2E

| Library | Lib Description | Abun | Pct Abun |
|---|---|---|---|
| HNT2RAT01 | hNT2 cell line, teratocarcinoma, treated RA | 4 | 0.0752 |
| TESTNOT01 | testis, 37 M | 1 | 0.0478 |
| PITUNOT01 | pituitary, 16-70 M/F | 1 | 0.0472 |
| COLNNOT07 | colon, 60 M | 1 | 0.0409 |
| LPARNOT02 | parotid gland, 70 M | 1 | 0.0324 |
| PROSTUT01 | prostate tumor, 50 M, match to PROSNOT02 | 1 | 0.0310 |
| UTRSNOT10 | uterus, endometrium, 50 F | 1 | 0.0292 |
| LUNGNOT12 | lung, 78 M | 1 | 0.0278 |
| SINTNOT13 | small intestine, ileum, ulcerative colitis, 25 F | 1 | 0.0275 |
| LUNGNOM01 | lung, 72 M, WM | 1 | 0.0267 |
| URETTUT01 | ureter tumor, 69 M | 1 | 0.0262 |
| LUNGNOT10 | lung, fetal M | 1 | 0.0261 |
| LIVRTUT01 | liver tumor, metastasis, 51 F | 1 | 0.0259 |
| BRSTNOM02 | breast, F, NORM, WM | 1 | 0.0206 |
| HNT3AZT01 | hNT2 cell line, teratocarcinoma, treated AZ | 1 | 0.0191 |
| PROSNON01 | prostate, 28 M, NORM | 2 | 0.0188 |
| LUNGFEM01 | lung, fetal, NORM, WM | 1 | 0.0148 |
| SMCANOT01 | smooth muscle cell line, aorta, M | 1 | 0.0136 |
| PROSNOT16 | prostate, 68 M | 1 | 0.0132 |
| TESTNOT03 | testis, 37 M | 1 | 0.0129 |
| BRSTNOT02 | breast, 55 F, match to BRSTTUT01 | 1 | 0.0111 |
| OVARTUT01 | ovarian tumor, 43 F, match to OVARNOT03 | 1 | 0.0103 |
| MELANOM01 | melanocytes, M, NORM, WM | 1 | 0.0096 |
| CARDFEM01 | heart, fetal, NORM, WM | 1 | 0.0083 |
| LIVSFEM02 | liver/spleen, fetal M, NORM, WM | 1 | 0.0026 |

Electronic Northern Results returned a total of 25 row(s).

FIGURE 3

SERINE/THREONINE PROTEIN KINASE

This application is a divisional application of U.S. application Ser. No. 08/818,024, filed Mar. 14, 1997 now U.S. Pat. No. 5,965,365.

FIELD OF THE INVENTION

This invention relates to nucleic acid and amino acid sequences of a novel serine/threonine protein kinase and to the use of these sequences in the diagnosis, prevention, and treatment of cancer and smooth muscle disorders.

BACKGROUND OF THE INVENTION

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate which drives activation is generally transferred from adenosine triphosphate molecules (ATP) to a particular protein by protein kinases and removed from that protein by protein phosphatases.

Phosphorylation occurs in response to extracellular signals (hormones, neurotransmitters, growth and differentiation factors, etc.), cell cycle checkpoints, and environmental or nutritional stresses, and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. Kinases are usually named after their substrates, or regulatory molecules, or after some aspect of a mutant phenotype. With regard to substrates, the protein kinases may be roughly divided into two groups those that phosphorylate tyrosine residues (protein tyrosine kinases (PTK) and those that phosphorylate serine or threonine residues (serine/threonine kinases (STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with a target protein. The primary structure of the kinase domain is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic ADPribose, arachidonic acid, and diacylglycerol. The cAMP dependent protein kinases (PKAs) are important members of the STK family. cAMP is an intracellular mediator of hormone action in all procaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cAMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, Vol. I and II:416–431, 1887 McGraw-Hill, New York, N.Y.).

The mitogen-activated protein (MAP) kinases are also members of the STK family. MAP kinases also regulate intracellular signaling pathways and mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) Nature 365:781–783). MAP kinase signaling pathways are present in mammalian cells as well as in yeast. Extracellular stimuli which activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1). Altered MAP kinase expression can therefore be implicated in a variety of disease conditions including cancer, inflammation, immune disorders, and disorders affecting growth and development.

The discovery of polynucleotides encoding SERINE/THREONINE protein kinases and the molecules themselves provide a means to investigate cell proliferation and differentiation under normal and disease conditions. Discovery of a novel SERINE/THREONINE protein kinase satisfies a need in the art by providing new compositions useful in the diagnosis and treatment of cancer and smooth muscle disorders.

SUMMARY OF THE INVENTION

The present invention features a novel human serine/threonine protein kinase hereinafter designated HSTPK and characterized as having similarity to serine/threonine protein kinases.

Accordingly, the invention features a substantially purified HSTPK having the amino acid sequence shown in SEQ ID NO:1.

One aspect of the invention features isolated and substantially purified polynucleotides that encode HSTPK. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under stringent conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode HSTPK. The present invention also features antibodies which bind specifically to HSTPK, and pharmaceutical compositions comprising substantially purified HSTPK. The invention also features the use of agonists and antagonists of HSTPK. The invention also provides methods for producing HSTPK and for treating disorders associated with expression of HSTPK.

BRIEF DESCRIPTION OF THE FIGURES

FIGS. 1A, 1B, 1C and 1D show the amino acid sequence (SEQ ID NO:1) and nucleic acid sequence (SEQ ID NO:2) of HSTPK. The alignment was produced using MACNASIS PRO software (Hitachi Software Engineering Co., Ltd., San Bruno, Calif.).

FIGS. 2A, 2B, 2C, 2D and 2E show the amino acid sequence alignments between HSTPK (SEQ ID NO:1) and STKs from C. elegans (GI 1246460; SEQ ID NO:3), D. melanogaster (GI 757823; SEQ ID NO:4), and man (GI 1669685; SEQ ID NO:5). The alignment was produced using the multisequence alignment program of DNASTAR™ software (DNASTAR Inc, Madison Wis.).

FIG. 3 shows the northern analysis for SEQ ID NO:2. The northern analysis was produced electronically using the LIFESEQ database (Incyte Pharmaceuticals, Inc., Palo Alto, Calif.).

DESCRIPTION OF THE INVENTION

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

HSTPK, as used herein, refers to the amino acid sequences of substantially purified HSTPK obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR (Perkin Elmer, Norwalk, Conn.) in the 5' and/or the 3' direction and resequenced, or which has been assembled from the overlapping sequences of more than one Incyte clone using the GELVIEW fragment assembly system (GCG, Madison, Wis.), or which has been both extended and assembled.

A "variant" of HSTPK, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic HSTPK, or any oligopeptide thereof, to induce a specific immune response in appropriate animals or cells and to bind with specific antibodies.

The term "agonist", as used herein, refers to a molecule which, when bound to HSTPK, causes a change in HSTPK which modulates the activity of HSTPK. Agonists may include proteins, nucleic acids, carbohydrates, or any other molecules which bind to HSTPK.

The terms "antagonist" or "inhibitor", as used herein, refer to a molecule which, when bound to HSTPK, blocks or modulates the biological or immunological activity of HSTPK. Antagonists and inhibitors may include proteins, nucleic acids, carbohydrates, or any other molecules which bind to HSTPK.

The term "modulate", as used herein, refers to a change or an alteration in the biological activity of HSTPK. Modulation may be an increase or a decrease in protein activity, a change in binding characteristics, or any other change in the biological, functional or immunological properties of HSTPK.

The term "mimetic", as used herein, refers to a molecule, the structure of which is developed from knowledge of the structure of HSTPK or portions thereof and, as such, is able to effect some or all of the actions of STK-like molecules.

The term "derivative", as used herein, refers to the chemical modification of a nucleic acid encoding HSTPK or the encoded HSTPK. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human HSTPK and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding HSTPK or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding HSTPK in a sample and thereby correlates with expression of the transcript from the polynucleotide encoding the protein.

"Alterations" in the polynucleotide of SEQ ID NO:2, as used herein, comprise any alteration in the sequence of polynucleotides encoding HSTPK including deletions, insertions, and point mutations that may be detected using hybridization assays. Included within this definition is the detection of alterations to the genomic DNA sequence which encodes HSTPK (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the polynucleotide sequence encoding HSTPK (e.g., using fluorescent in situ hybridization [FISH] to metaphase chromosomes spreads).

As used herein, the term "antibody" refers to intact molecules as well as fragments thereof, such as Fab F(ab')$_2$, and Fv, which are capable of binding the epitopic determinant. Antibodies that bind HSTPK polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of a novel human serine/threonine protein kinase (HSTPK), the polynucleotides encoding HSTPK, and the use of these compositions for the diagnosis, prevention, and treatment of cancer and smooth muscle disorders.

Nucleic acids encoding the human HSTPK of the present invention were first identified in Incyte Clone 94712 from the pituitary gland cDNA library PITUNOT01 through a computer-generated search for amino acid sequence alignments. A consensus sequence, SEQ ID NO:2, was derived from extension and resequencing of this clone.

In one embodiment, the invention encompasses a polypeptide comprising the amino acid sequence of SEQ ID NO:1, as shown in FIGS. 1A, 1B, 1C and 1D. HSTPK is 377 amino acids in length and has potential glycosylation sites at N202 and N363. Cysteine residues, representing potential cysteine-cysteine disulfide bridging sites are located at C34, C71, C83, C109, C148, C171, 236, C290, and C225. As shown in FIGS. 2A, 2B, 2C, 2D and 2E, HSTPK has chemical and structural homology with STK from *C. elegans* (GI 1246460; SEQ ID NO:3), *D. melanogaster* (GI 757823; SEQ ID NO:4), and man (GI 1669685; SEQ ID NO:5) In particular, HSTPK and shares 67% and 36% identity with STK from *C. elegans* and *D. melanogaster*, respectively, and 98% identity with the human STK. In addition, HSTPK shares four key amino acid motifs associated with the protein kinase catalytic subdomains. The sequence HCDLKPEN beginning at H82 is located in subdomain VIB and is recognized as important in catalysis of the phosphate transfer from ATP to serine or threonine during protein phosphorylation. The sequence KXXDFG beginning at K101 is located in subdomain VII and functions in the orientation of ATP for phosphate transfer. The sequence YIQSRFYRSPE beginning at Y118 is located in subdomain VIII, and is generally well conserved in different protein kinase families. D138 is a nearly invariant aspartic acid residue in domain IX of protein kinase that functions in stabilizing the catalytic loop. Each of these four sequences is shared by the STK's from *C. elegans* and *D. melanogaster*. The glycosylation site at N202 is shared in the human STK, and all of the cysteine residues are shared by one or more of the three STK's shown. Northern analysis (FIG. 3) shows the expression of this sequence in various libraries, 30% of which are immortalized or cancerous and 40% of which involve various smooth muscle tissues.

The invention also encompasses HSTPK variants. A preferred HSTPK variant is one having at least 80%, and more preferably 90%, amino acid sequence identity to the HSTPK amino acid sequence (SEQ ID NO:1). A most preferred HSTPK variant is one having at least 95% amino acid sequence identity to SEQ ID NO:1.

The invention also encompasses polynucleotides which encode HSTPK. Accordingly, any nucleic acid sequence which encodes the amino acid sequence of HSTPK can be used to generate recombinant molecules which express HSTPK. In a particular embodiment, the invention encompasses the polynucleotide comprising the nucleic acid sequence of SEQ ID NO:2 as shown in FIGS. 1A, 1B and 1C.

It will be appreciated by those skilled in the art that as a result of the degeneracy of the genetic code, a multitude of nucleotide sequences encoding HSTPK, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HSTPK, and all such variations are to be considered as being specifically disclosed.

Although nucleotide sequences which encode HSTPK and its variants are preferably capable of hybridizing to the nucleotide sequence of the naturally occurring HSTPK under appropriately selected conditions of stringency, it may be advantageous to produce nucleotide sequences encoding HSTPK or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HSTPK and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode HSTPK and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding HSTPK or any portion thereof.

Also encompassed by the invention are polynucleotide sequences that are capable of hybridizing to the claimed nucleotide sequences, and in particular, those shown in SEQ ID NO:2. under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding HSTPK which are encompassed by the invention include deletions, insertions, or substitutions of different nucleotides resulting in a polynucleotide that encodes the same or a functionally equivalent HSTPK. The encoded protein may also contain deletions, insertions, or substitutions of amino acid residues which produce a silent change and result in a functionally equivalent HSTPK. Deliberate amino acid substitutions may be made on the basis of similarity in polarity, charge, solubility, hydrophobicity, hydrophilicity, and/or the amphipathic nature of the residues as long as the biological activity of HSTPK is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding HSTPK. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE amplification system marketed by Gibco BRL (Gaithersburg, Md.). Preferably, the process is automated with machines such as the MICROLAB 2200 (Hamilton, Reno, Nev.), Peltier PTC 200 thermal cyclerc; MJ Research, Watertown, Mass.), and the ABI 377 DNA sequencers (Perkin Elmer).

The nucleic acid sequences encoding HSTPK may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk in genomic DNA (Clontech, Palo Alto, Calif.). This process avoids the need to screen libraries and is useful in finding intron/exon junctions.

When screening for fill-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HSTPK, or fusion proteins or functional equivalents thereof, may be used in recombinant DNA molecules to direct expression of HSTPK in appropriate host cells. Due to the inherent degeneracy of the genetic code, other DNA sequences which encode substantially the same or a finctionally equivalent amino acid sequence may be produced and these sequences may be used to clone and express HSTPK.

As will be understood by those of skill in the art, it may be advantageous to produce HSTPK-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally kcnown in the art in order to alter HSTPK encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding HSTPK may be ligated to a heterologous sequence to encode a fusion protein. For example, to screen peptide libraries for inhibitors of HSTPK activity, it may be useful to encode a chimeric HSTPK protein that can be recognized by a commercially available antibody. A fusion protein may also be engineered to contain a cleavage site located between the HSTPK encoding sequence and the heterologous protein sequence, so that HSTPK may be cleaved and purified away from the heterologous moiety.

In another embodiment, sequences encoding HSTPK may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of HSTPK, or a portion thereof. For example, peptide synthesis can be performed using various solid-phase techniques (Roberge, J. Y. et al. (1995) Science 269:202–204) and automated synthesis may be achieved, for example, using the ABI 431A peptide synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of HSTPK, or any part thereof, may be altered during direct synthesis and/or combined using chemical methods with sequences from other proteins, or any part thereof, to produce a variant polypeptide.

In order to express a biologically active HSTPK, the nucleotide sequences encoding HSTPK or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding HSTPK and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding HSTPK. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HSTPK, vectors based on SV40 or EBV may be used with an appropriate selectable marker.

In bacterial systems, a number of expression vectors may be selected depending upon the use intended for HSTPK. For example, when large quantities of HSTPK are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding HSTPK may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding HSTPK may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technolog* (1992) McGraw Hill, New York, N.Y.; pp. 191–196.

An insect system may also be used to express HSTPK. For example, in one such system, *Autographa califomica* nuclear polyhedrosis virus (AcNPV) is used as a vector to express foreign genes in *Spodoptera frugiperda* cells or in Trichoplusia larvae. The sequences encoding HSTPK may be cloned into a non-essential region of the virus, such as the polyhedrin gene, and placed under control of the polyhedrin promoter. Successful insertion of HSTPK will render the polyhedrin gene inactive and produce recombinant virus lacking coat protein. The recombinant viruses may then be used to infect, for example, *S. frugiperda* cells or Trichoplusia larvae in which HSTPK may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding HSTPK may be ligated into an adenovirus transcription/translation complex consisting of the late promoter and tripartite leader sequence. Insertion in a non-essential E1 or E3 region of the viral genome may be used to obtain a viable virus which is capable of expressing HSTPK in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding HSTPK. Such signals include the ATG initiation codon and adjacent sequences. In cases where sequences encoding HSTPK, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or finction. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express HSTPK may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr, which confers resistance to methotrexate (Wigler, M. et al. (1980) Proc. Natl. Acad. Sci 77:3567–70); npt, which confers resistance to the aminoglycosides neomycin and G-418 (Colbere-Garapin, F. et al (1981) J. Mol. Biol. 150:1–); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding HSTPK is inserted within a marker gene sequence, recombinant cells containing sequences encoding HSTPK can be identified by the absence of marker gene function. Alternatively, a marker gene can be placed in tandem with a sequence encoding HSTPK under the control of a single promoter. Expression of the marker gene in response to induction or selection usually indicates expression of the tandem gene as well.

Alternatively, host cells which contain the nucleic acid sequence encoding HSTPK and express HSTPK may be identified by a variety of procedures known to those of skill in the art. These procedures include, but are not limited to, DNA—DNA or DNA–RNA hybridizations and protein bioassay or immunoassay techniques which include membrane, solution, or chip based technologies for the detection and/or quantification of nucleic acid or protein.

The presence of polynucleotide sequences encoding HSTPK can be detected by DNA—DNA or DNA–RNA hybridization or amplification using probes or portions or fragments of polynucleotides encoding HSTPK. Nucleic acid amplification based assays involve the use of oligonucleotides or oligomers based on the sequences encoding HSTPK to detect transformants containing DNA or RNA encoding HSTPK. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of HSTPK, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HSTPK is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HSTPK include oligolabeling, nick translation, end-labeling or PCR amplification using a labeled nucleotide. Alternatively, the sequences encoding HSTPK, or any portions thereof may be cloned into a vector for the production of an MRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn (Kalamazoo, Mich.); Promega (Madison Wis.); and U.S. Biochemical Corp. (Cleveland, Ohio)). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding HSTPK may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode HSTPK may be designed to contain signal sequences which direct secretion of HSTPK through a prokaryotic or eukaryotic cell membrane. Other recombinant constructions may be used to join sequences encoding HSTPK to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HSTPK may be used to facilitate purification. One such expression vector provides for expression of a fusion protein containing HSTPK and a nucleic acid encoding 6 histidine residues preceding a thioredoxin or an enterokinase cleavage site. The histidine residues facilitate purification on IMIAC (immobilized metal ion affinity chromatography), as described in Porath, J. et al. (1992, Prot. Exp. Purif. 3:263–281) while the enterokinase cleavage site provides a means for purifying HSTPK from the fusion protein. A discussion of vectors which contain fusion proteins is provided in Kroll, D. J. et al. (1993; DNA Cell Biol. 12:441–453).

In addition to recombinant production, fragments of HSTPK may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using an Applied Biosystems 431A peptide synthesizer (Perkin Elmer). Various fragments of HSTPK may be chemically synthesized separately and combined using chemical methods to produce the full length molecule.

THERAPEUTICS

Chemical and structural homology exists among HSTPK and STKs from C. elegans, D. melanogaster, and man. In addition, northern analysis shows that HSTPK is expressed in immortalized cell lines and in cancer and various normal and diseased smooth muscle tissues. Therefore HSTPK appears to be associated with the development of cancer and smooth muscle disorders. In particular, increased expression or activity of HSTPK may be associated with the development of cancer, and decreased expression or activity of HSTPK may be associated with smooth muscle disorders.

Therefore, in one embodiment, HSTPK or a fragment or derivative thereof may be administered to a subject to treat a smooth muscle disorder. A smooth muscle disorder is defined as any impairment or alteration in the normal action of smooth muscle and may include, but is not limited to, hypertension, myocardial infraction, cardiovascular shock, angina, arrhythmias, asthma, and migraine. Types of smooth muscle include blood vessels, gastrointestinal tract, esophagus, cardiac smooth muscle, lungs, and uterus.

In another embodiment, a vector capable of expressing HSTPK, or a fragment or a derivative thereof, may also be administered to a subject to treat a smooth muscle disorder and, in particular, those listed above.

In another embodiment, the complement of the polynucleotide encoding HSTPK or an antisense molecule may be administered to a subject to treat or prevent cancer such as adenocarcinoma, sarcoma, melanoma, lymphoma, leukemia, and myeloma. In particular, cancers may include, but are not limited to, cancer of the testis, colon, prostate, uterus, lung, intestine colon, liver, breast, skin, heart, and spleen.

In another embodiment, antagonists or inhibitors of HSTPK may be administered to a subject to treat or prevent the types of cancer listed above. In one aspect, antibodies which are specific for HSTPK may be used directly as an antagonist, or indirectly as a targeting or delivery mechanism for bringing a pharmaceutical agent to cells or tissue which express HSTPK.

In other embodiments, any of the therapeutic proteins, antagonists, antibodies, agonists, antisense sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of HSTPK may be produced using methods which are generally known in the art. In particular, purified HSTPK may be used to produce antibodies or to screen libraries of pharmaceutical agents to identify those which specifically bind HSTPK.

The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HSTPK or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to HSTPK have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of HSTPK amino acids may be fused with those of another protein such as keyhole limpet hemocyanin and antibody produced against the chimeric molecule.

Monoclonal antibodies to HSTPK may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce HSTPK-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments which contain specific binding sites for HSTPK may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HSTPK and its specific antibody. A two-site, monoclonal-based immunoassay utilizing monoclonal antibodies reactive to two non-interfering HSTPK epitopes is preferred, but a competitive binding assay may also be employed (Maddox, supra).

In another embodiment of the invention, the polynucleotides encoding HSTPK, or any fragment thereof, or antisense molecules, may be used for therapeutic purposes. In one aspect, antisense to the polynucleotide encoding HSTPK may be used in situations in which it would be desirable to block the transcription of the mRNA. In particular, cells may be transformed with sequences complementary to polynucleotides encoding HSTPK. Thus, antisense molecules may be used to modulate HSTPK activity, or to achieve regulation of gene function. Such technology is now well known in the art, and sense or antisense oligomers or larger fragments, can be designed from various locations along the coding or control regions of sequences encoding HSTPK.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding HSTPK. These techniques are described both in Sambrook et al. (supra) and in Ausubel et al. (supra).

Genes encoding HSTPK can be turned off by transforming a cell or tissue with expression vectors which express high levels of a polynucleotide or fragment thereof which encodes HSTPK. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding HSTPK, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HSTPK.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HSTPK. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HSTPK, antibodies to HSTPK, mimetics, agonists, antagonists, or inhibitors of HSTPK. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HSTPK, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HSTPK or fragments thereof, antibodies of HSTPK, agonists, antagonists or inhibitors of HSTPK, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxics to the therapeutic effects is the therapeutic index, which can be expressed as the ratio LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HSTPK may be used for the diagnosis of conditions or diseases characterized by expression of HSTPK, or in assays to monitor patients being treated with HSTPK, agonists, antagonists or inhibitors. The antibodies useful for diagnostic purposes may be prepared in the same manner as those described above for therapeutics. Diagnostic assays for HSTPK include methods which utilize the antibody and a label to detect HSTPK in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HSTPK are known in the art and provide a basis for diagnosing altered or abnormal levels of HSTPK expression. Normal or standard values for HSTPK expression are established by combining body fluids or cell extracts taken from normal mammalian subjects, preferably human, with antibody to HSTPK under conditions suitable for complex formation. The amount of standard complex formation may be quantified by various methods, but preferably by photometric, means. Quantities of HSTPK expressed in subject samples from biopsied tissues are compared with the standard values. Deviation between standard and subject values establishes the parameters for diagnosing disease.

In another embodiment of the invention, the polynucleotides encoding HSTPK may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of HSTPK may be correlated with disease. The diagnostic assay may be used to distinguish between absence, presence, and excess expression of HSTPK, and to monitor regulation of HSTPK levels during therapeutic intervention.

In one aspect, hybridization with PCR probes which are capable of detecting polynucleotide sequences, including genomic sequences, encoding HSTPK or closely related molecules, may be used to identify nucleic acid sequences which encode HSTPK. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HSTPK, alleles, or related sequences.

Probes may also be used for the detection of related sequences, and should preferably contain at least 50% of the nucleotides from any of the HSTPK encoding sequences. The hybridization probes of the subject invention may be DNA or RNA and derived from the nucleotide sequence of SEQ ID NO:2 or from genomic sequence including promoter, enhancer elements, and introns of the naturally occurring HSTPK.

Means for producing specific hybridization probes for DNAs encoding HSTPK include the cloning of nucleic acid sequences encoding HSTPK or HSTPK derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HSTPK may be used for the diagnosis of conditions or diseases which are associated with expression of HSTPK. Examples of such conditions or diseases include smooth muscle disorders such as hypertension, myocardial infraction, cardiovascular shock, angina, arrhythmias, asthma, and migraine; and cancers such as cancer of the testis, colon, prostate, uterus, lung, intestine colon, liver, breast, skin, heart, and spleen. The polynucleotide sequences encoding HSTPK may be used in Southern or northern analysis, dot blot, or other membrane-based technologies; in PCR technologies; or in dip stick, pin, ELISA or chip assays utilizing fluids or tissues from patient biopsies to detect altered HSTPK expression. Such qualitative or quantitative methods are well known in the art.

In a particular aspect, the nucleotide sequences encoding HSTPK may be useful in assays that detect activation or induction of various cancers, particularly those mentioned above. The nucleotide sequences encoding HSTPK may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding HSTPK in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HSTPK, a normal or standard profile for expression is established. This may be accomplished by combining body fluids or cell extracts taken from normal subjects, either animal or human, with a sequence, or a fragment thereof, which encodes HSTPK, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HSTPK may involve the use of PCR. Such oligomers may be chemically synthesized, generated enzymatically, or produced from a recombinant source. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HSTPK include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–235. The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode HSTPK may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding HSTPK on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HSTPK, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HSTPK and the agent being tested, may be measured.

Another technique for drug screening which may. be used provides for high throughput screening of compounds having suitable binding affinity to the protein of interest as described in published PCT application WO84/03564. In this method, as applied to HSTPK large numbers of different small test compounds are synthesized on a solid substrate, such as plastic pins or some other surface. The test compounds are reacted with HSTPK, or fragments thereof, and washed. Bound HSTPK is then detected by methods well known in the art. Purified HSTPK can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HSTPK specifically compete with a test compound for binding HSTPK. In this manner, the antibodies can be used to detect the presence of any peptide which shares one or more antigenic determinants with HSTPK.

In additional embodiments, the nucleotide sequences which encode HSTPK may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I PITUNOT01 cDNA Library Construction

The pituitary library (PITUNOT01) was constructed from a pooled sample of 21 whole, normal pituitary glands from human brains of Caucasian males and females with a range of ages from 16–70 years. The poly A+RNA was obtained from Clontech Laboratories Inc. (catalog #6584-1 and #6584-2, 4030 Fabian Way, Palo Alto Calif.)

A cDNA library was custom constructed using this poly A RNA (Stratagene, La Jolla Calif.). cDNA synthesis was prepared using both oligo d(T) and random hexamers, and the two preparations were treated separately. Synthetic adapter oligonucleotides were ligated onto cDNA ends enabling insertion into the Stratagene UNIZAP vector system. Finally, the two cDNA preparations were combined into a single library by mixing equal numbers of bacteriophage.

The pituitary cDNA library can be screened with either DNA probes or antibody probes, and the PBLUESCRIPT phagemid (Stratagene) can be rapidly excised in vivo. The custom-constructed library phage particles were infected into *E. coli* host strain XL1-BLUE (Stratagene) which has a high transformation efficiency. This efficiency increases the probability of obtaining rare, under-represented clones in the cDNA library. Alternative unidirectional vectors include, but are not limited to, pcDNAI (Invitrogen, San Diego Calif.) and pSHlox-1 (Novagen, Madison Wis.).

II Isolation and Sequencing of cDNA Clones

The phagemid forms of individual cDNA clones were obtained by the in vivo excision process, in which the host bacterial strain was co-infected with both the library phage and an f1 helper phage. Polypeptides or enzymes derived from both the library-containing phage and the helper phage nicked the DNA, initiated new DNA synthesis from defined sequences on the target DNA, and created a smaller, single stranded circular phagemid DNA molecule that included all DNA sequences of the pBluescript phagemid and the cDNA insert. The phagemid DNA was released from the cells, purified, and used to reinfect fresh host cells (SOLR, Stratagene) where double-stranded phagemid DNA was produced. Because the phagemid carries the gene for beta-lactamase, the newly transformed bacteria were selected on medium containing ampicillin.

Alternatively, phagemid DNA is purified using the QIAWELL-8plasmid purification system (QIAGEN Inc, Chatsworth Calif.). The DNA was eluted from the purification resin and prepared for DNA sequencing and other analytical manipulations.

The cDNAs were sequenced by the method of Sanger et al. (1975, J. Mol. Biol. 94:441f), using a Hamilton MICROLAB 2200 (Hamilton, Reno, Nev.) in combination with Peltier PTC200 from thermal cyclers (MJ Research, Watertown, Mass.)) and Applied Biosystems 377 DNA Sequencing Systems.

III Homology Searching of cDNA Clones and Their Deduced Proteins

Each cDNA was compared to sequences in GenBank using a search algorithm developed by Applied Biosystems and incorporated into the INHERIT 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT 620 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as the GenBank or LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HSTPK occurs. Abundance and percent abundance are also reported. Abundance directly reflects the number of times a particular transcript is represented in a cDNA library, and percent abundance is abundance divided by the total number of sequences examined in the cDNA library.

V Extension of HSTPK-Encoding Polynucleotides

Nucleic acid sequence of Incyte Clone 94712 or SEQ ID NO:2 is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier PTC200thermal cycler; (M.J. Research, Watertown, Mass.) and the following parameters:

| Step 1 | 94° C. for 1 min (initial denaturation) |
| --- | --- |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent *E. coli* cells (in 40 µl of appropriate media) are transformed with 3 µl of ligation mixture and cultured in 80 µl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 µl of liquid LB/2× Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer, and one or both of the gene specific primers used for the extension reaction are added to each well. Amplification is performed using the following conditions:

| Step 1 | 94° C. for 60 sec |
| --- | --- |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 software (National Biosciences), labeled by combining 50 pmol of each oligomer and 250 µCi of [$\gamma$-$^{32}$P] adenosine triphosphate (Amersham) and T4 polynucleotide kinase (DuPont NEN, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (NYTRAN Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots on the blots are exposed to in a Phosphoimager cassette (Molecular Dynamics, Sunnyvale, Calif.) for several hours, hybridization patterns are compared visually.

VII Antisense Molecules

Antisense molecules or polynucleotides complementary to the HSTPK-encoding sequence, or any part thereof, is used to inhibit in vivo or in vitro expression of naturally occurring HSTPK. Although use of antisense oligonucleotides, comprising about 20 base-pairs, is specifically described, essentially the same procedure is used with larger cDNA fragments. An oligonucleotide based on the coding sequences of HSTPK, as shown in FIGS. 1A, 1B, 1C, and 1D is used to inhibit expression of naturally occurring HSTPK. The complementary oligonucleotide is designed from the most unique 5' sequence as shown in FIGS. 1A, 1B, 1C and 1D and used either to inhibit transcription by preventing promoter binding to the upstream nontranslated sequence or translation of an HSTPK-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIGS. 1A, 1B, 1C, and 1D.

VIII Expression of HSTPK

Expression of HSTPK is accomplished by subcloning the cDNAs into appropriate vectors and transforming the vectors into host cells. In this case, the cloning vector, pSport, previously used for the generation of the cDNA library is used to express HSTPK in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HSTPK into the bacterial growth media which can be used directly in the following assay for activity.

IX Demonstration of HSTPK Activity

HSTPK activity may be measured by phosphorylation of a protein substrate using gamma-labeled $^{32}$P-ATP and quantitation of the incorporated radioactivity using a gamma radioisotope counter. HSTPK is incubated with the protein substrate, $^{32}$P-ATP, and a kinase buffer. The $^{32}$P incorporated into the substrate is then separated from free $^{32}$P-ATP by electrophoresis and the incorporated $^{32}$P is counted. A determination of the specific amino acid residues phosphorylated is made by phosphoamino acid analysis of the hydrolyzed protein.

X Production of HSTPK Specific Antibodies

HSTPK that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an ABI Model 431A peptide synthesizer using fmoc-chemistry, and coupled to keyhole limpet hemocyanin (KLH) (Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HSTPK Using Specific Antibodies

Naturally occurring or recombinant HSTPK is substantially purified by immunoaffinity chromatography using antibodies specific for HSTPK. An immunoaffinity column is constructed by covalently coupling HSTPK antibody to an activated chromatographic resin, such as CnBr-activated EPHAROSE (Pharmacia & Upjohn). After the coupling, the resin is blocked and washed according to the manufacturer's instructions.

Media containing HSTPK is passed over the immunoaffinity column, and the column is washed under conditions that allow the preferential absorbance of HSTPK (e.g., high ionic strength buffers in the presence of detergent). The column is eluted under conditions that disrupt antibody/HSTPK binding (eg, a buffer of pH 2–3 or a high concentration of a chaotrope, such as urea or thiocyanate ion), and HSTPK is collected.

XII Identification of Molecules Which Interact with HSTPK

HSTPK or biologically active fragments thereof are labeled with $^{125}$I Bolton-Hunter reagent (Bolton et al. (1973) Biochem. J. 133:529). Candidate molecules previously arrayed in the wells of a multi-well plate are incubated with the labeled HSTPK, washed and any wells with labeled HSTPK complex are assayed. Data obtained using different concentrations of HSTPK are used to calculate values for the number, affinity, and association of HSTPK with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A substantially purified serine/threonine protein kinase polypeptide selected from the group consisting of:
   a) a polypeptide comprising the amino acid sequence depicted in SEQ ID NO:1,
   b) a polypeptide having at least 90% sequence identity over the entire lenath of the amino acid sequence depicted in SEQ ID NO:1, wherein said polypeptide has serine/threonine protein kinase activity, and
   c) a fragment of the polypeptide depicted in SEQ ID NO:1, wherein said fragment has serine/threonine protein kinase activity.

2. The polypeptide of claim 1, wherein said peptide has the amino acid sequence depicted in SEQ ID NO:1.

3. A composition comprising the polypeptide of claim 1 in conjunction with a suitable pharmaceutical carrier.

4. A composition comprising the polypeptide of claim 2 in conjunction with a suitable pharmaceutical carrier.

5. An immunologically-active fragment of the serine/threonine kinase polypeptide depicted in SEQ ID NO:1, wherein said fragment generates an antibody that specifically binds to the polypeptide depicted in SEQ ID NO:1.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 376 amino acids
      (B) TYPE: amino acid
      (C) STRANDEDNESS: single
      (D) TOPOLOGY: linear (vii) IMMEDIATE SOURCE:
      (A) LIBRARY: Consensus
      (B) CLONE: 94712

(xi) SEQUENCE DESCRIPTION: SEQ ID NO: 1:

```
Met Glu Leu Lys Ile Leu Glu Ala Leu Arg Lys Lys Asp Lys Asp Asn
 1               5                  10                  15

Thr Tyr Asn Val Val His Met Lys Asp Phe Phe Tyr Phe Arg Asn His
                20                  25                  30

Phe Cys Ile Thr Xaa Glu Leu Leu Gly Ile Asn Leu Phe Glu Leu Met
            35                  40                  45

Lys Asn Asn Asn Phe Gln Gly Phe Ser Leu Ser Ile Val Arg Gly Phe
```

```
              50                  55                  60
Thr Leu Ser Xaa Xaa Gly Cys Leu Gln Met Leu Ser Val Glu Lys Ile
 65                  70                  75                  80

Ile His Cys Asp Leu Lys Pro Glu Asn Ile Val Leu Tyr Gln Lys Gly
                 85                  90                  95

His Ala Ser Val Lys Val Xaa Asp Phe Gly Ser Ser Cys Tyr Glu His
                100                 105                 110

Gln Lys Val Tyr Thr Tyr Ile Gln Ser Arg Phe Tyr Arg Ser Pro Glu
                115                 120                 125

Val Ile Leu Gly His Pro His Pro Tyr Asp Val Ala Ile Asp Met Trp
130                 135                 140

Ser Leu Gly Cys Ile Thr Ala Glu Leu Tyr Thr Gly Tyr Pro Leu Phe
145                 150                 155                 160

Pro Gly Glu Asn Glu Val Glu Gln Leu Ala Cys Ile Met Glu Val Leu
                165                 170                 175

Gly Leu Pro Pro Ala Gly Phe Ile Gln Thr Ala Ser Arg Arg Gln Thr
                180                 185                 190

Phe Phe Asp Ser Lys Gly Phe Pro Lys Asn Ile Thr Asn Asn Arg Gly
                195                 200                 205

Lys Lys Arg Tyr Pro Asp Ser Lys Asp Leu Thr Met Val Leu Lys Thr
210                 215                 220

Tyr Asp Thr Ser Phe Leu Asp Phe Leu Arg Arg Cys Leu Val Trp Glu
225                 230                 235                 240

Pro Ser Leu Arg Met Thr Pro Asp Gln Ala Leu Lys His Ala Trp Ile
                245                 250                 255

His Gln Ser Arg Asn Leu Lys Pro Gln Pro Arg Pro Gln Thr Leu Arg
                260                 265                 270

Lys Ser Asn Ser Phe Phe Pro Ser Glu Thr Arg Lys Asp Lys Val Gln
                275                 280                 285

Gly Cys His His Ser Ser Arg Lys Ala Asp Glu Ile Thr Lys Glu Thr
290                 295                 300

Thr Glu Lys Thr Lys Asp Ser Pro Thr Lys His Val Gln His Ser Gly
305                 310                 315                 320

Asp Gln Gln Asp Cys Leu Gln His Gly Ala Asp Thr Val Gln Leu Pro
                325                 330                 335

Gln Leu Val Asp Ala Pro Lys Lys Ser Glu Ala Ala Val Gly Ala Glu
                340                 345                 350

Val Ser Met Thr Ser Pro Gly Gln Ser Lys Asn Phe Ser Leu Lys Asn
355                 360                 365

Thr Asn Val Leu Pro Pro Ile Val
370                 375

(2) INFORMATION FOR SEQ ID NO: 2:

(i) SEQUENCE CHARACTERISTICS:
        (A) LENGTH: 1498 base pairs
        (B) TYPE: nucleic acid
        (C) STRANDEDNESS: single
        (D) TOPOLOGY: linear (vii) IMMEDIATE SOURCE:
        (A) LIBRARY: Consensus
        (B) CLONE: 94712

(xi) SEQUENCE DESCRIPTION: SEQ ID NO: 2:

GTCCTTTGGG ACAGGTGGCC AAGTGCTTGG ATCACAAAAA CAATGAGCTG GTGGCCCTGA     60
```

-continued

```
AAATCATCAG GAACAAGAAG AGGTTTCACC AGCAGGCCCT GATGGAGCTG AAGATCCTGG      120

AAGCTCTCAG AAAGAAGGAC AAAGACAACA CCTACAATGT GGTGCATATG AAGGACTTTT      180

TCTACTTTCG CAATCACTTC TGCATCACCT NNGAGCTCCT GGGAATCAAC TTGTTTGAGT      240

TGATGAAGAA TAACAACTTT CAAGGCTTCA GTCTGTCCAT AGTTCGGGGC TTCACTCTCT      300

CTGNNNGGGG GTGCTTGCAG ATGCTTTCGG TAGAGAAAAT CATTCACTGT GATCTCAAGC      360

CCGAAAATAT AGTGCTATAC CAAAAGGGCC ACGCCTCTGT TAAAGTCANT GACTTTGGAT      420

CAAGCTGTTA TGAACACCAG AAAGTATACA CGTACATCCA AAGCCGGTTC TACCGATCCC      480

CAGAAGTAAT CCTGGGCCAC CCACACCCCT ACGACGTGGC CATTGACATG TGGAGCCTGG      540

GCTGCATCAC GGCGGAGTTG TACACGGGCT ACCCCCTGTT CCCCGGGGAG AATGAGGTGG      600

AGCAGCTGGC CTGCATCATG GAGGTGCTGG GTCTGCCGCC AGCCGGCTTC ATTCAGACAG      660

CCTCCAGGAG ACAGACATTC TTTGATTCCA AGGTTTTCC TAAAAATATA ACCAACAACA       720

GGGGAAAAA AAGATACCCA GATTCCAAGG ACCTCACGAT GGTGCTGAAA ACCTATGACA       780

CCAGCTTCCT GGACTTTCTC AGAAGGTGTT TGGTATGGGA ACCTTCTCTT CGCATGACCC      840

CGGACCAGGC CCTCAAGCAT GCTTGGATTC ATCAGTCTCG GAACCTCAAG CCACAGCCCA      900

GGCCCCAGAC CCTGAGGAAA TCCAATTCCT TTTTCCCCTC TGAGACAAGG AAGGACAAGG      960

TTCAAGGCTG TCATCACTCG AGCAGAAAAG CAGATGAGAT CACCAAAGAG ACTACAGAGA     1020

AAACAAAAGA TAGCCCCACG AAGCATGTTC AGCATTCAGG TGATCAGCAG GACTGTCTCC     1080

AGCACGGAGC TGACACTGTT CAGCTGCCTC AACTGGTAGA CGCTCCCAAG AAGTCAGAGG     1140

CAGCTGTCGG GGCGGAGGTG TCCATGACCT CCCCAGGACA GAGCAAAAAC TTCTCCCTCA     1200

AGAACACAAA CGTTTTACCC CCTATTGTAT GACCTTTGCT GAGGGTATGT CCTGCTCCTT     1260

TCCACCAGTG ATTTGTATTA AGACAGCACT TATATTGTAC AATACTTCAG ACTGTTTTTT     1320

TTAAATACAT AAAACTTTAT GTTAAAAAAC TCTATTAACA TGGCCAATTG GCATGACTCC     1380

TCTTATGAGG GATGGGGAG GATGTCCTTG CACTTAAACT CATTCCATAT GCATCTGTGT      1440

GTGTAGAGGG GGCGGGTAGT TTTGAACTCT CAGTGTTACA GCATCATTAA TGGAACTC       1498
```

(2) INFORMATION FOR SEQ ID NO: 3:

(i) SEQUENCE CHARACTERISTICS:
        (A) LENGTH: 508 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1246460

(xi) SEQUENCE DESCRIPTION: SEQ ID NO: 3:

```
Met Thr Leu Phe Glu Pro Ser Thr Ser Gly Asn Arg Met Gly Tyr Arg
 1               5                  10                  15

Gly Ser Ser Asn Ser Ser Ser Gly Val Gly Ser Gly Gly Ser Gly Ser
                20                  25                  30

Leu Met Thr Gln Ser Ile Gly Gly Pro Asn Lys His Leu Ser Ala Ser
            35                  40                  45

His Ser Thr Leu Asn Thr Ala Ser Thr His Asp Met Met His Ser Lys
        50                  55                  60

Ile Pro Lys Ser Pro Ser Asn Glu Ser Leu Ser Arg Ser His Thr Ser
65                  70                  75                  80

Ser Ser Gly Gly Ser Gln Gly Gly His Asn Ser Asn Ser Gly Ser Asn
```

-continued

```
            85                  90                  95
Ser Gly Phe Arg Pro Glu Asp Ala Val Gln Thr Phe Gly Ala Lys Leu
                100                 105                 110
Val Pro Phe Glu Lys Asn Glu Ile Tyr Asn Tyr Thr Arg Val Phe Phe
            115                 120                 125
Val Gly Ser His Ala Lys Lys Gln Ala Gly Val Ile Gly Gly Ala Asn
        130                 135                 140
Asn Gly Gly Tyr Asp Asp Glu Asn Gly Ser Tyr Gln Leu Val Val His
145                 150                 155                 160
Asp His Ile Ala Tyr Arg Tyr Glu Val Leu Lys Val Ile Gly Lys Gly
                165                 170                 175
Ser Phe Gly Gln Val Ile Lys Ala Phe Asp His Lys Tyr Gln Gln Tyr
            180                 185                 190
Val Ala Leu Lys Leu Val Arg Asn Glu Lys Arg Phe His Arg Gln Ala
            195                 200                 205
Asp Glu Glu Ile Arg Ile Leu Asp His Leu Arg Arg Gln Asp Ser Asp
        210                 215                 220
Gly Thr His Asn Ile Ile His Met Leu Asp Tyr Phe Asn Phe Arg Asn
225                 230                 235                 240
His Lys Cys Ile Thr Phe Glu Leu Leu Ser Ile Asn Leu Tyr Glu Leu
                245                 250                 255
Ile Lys Arg Asn Lys Phe Gln Gly Phe Ser Leu Met Leu Val Arg Lys
            260                 265                 270
Phe Ala Tyr Ser Met Leu Leu Cys Leu Asp Leu Leu Gln Lys Asn Arg
            275                 280                 285
Leu Ile His Cys Asp Leu Lys Pro Glu Asn Val Leu Leu Lys Gln Gln
        290                 295                 300
Gly Arg Ser Gly Ile Lys Val Ile Asp Phe Gly Ser Ser Cys Phe Asp
305                 310                 315                 320
Asp Gln Arg Ile Tyr Thr Tyr Ile Gln Ser Arg Phe Tyr Arg Ala Pro
                325                 330                 335
Glu Val Ile Leu Gly Thr Lys Tyr Gly Met Pro Ile Asp Met Trp Ser
            340                 345                 350
Leu Gly Cys Ile Leu Ala Glu Leu Leu Thr Gly Tyr Pro Leu Leu Pro
            355                 360                 365
Gly Glu Asp Glu Asn Asp Gln Leu Ala Leu Ile Ile Glu Leu Leu Gly
        370                 375                 380
Met Pro Pro Lys Ser Leu Glu Thr Ala Lys Arg Ala Arg Thr Phe
385                 390                 395                 400
Ile Thr Ser Lys Gly Tyr Pro Arg Tyr Cys Thr Ala Thr Ser Met Pro
                405                 410                 415
Asp Gly Ser Val Val Leu Ala Gly Ala Arg Ser Lys Arg Gly Lys Met
            420                 425                 430
Arg Gly Pro Pro Ala Ser Arg Ser Trp Ser Thr Ala Leu Lys Asn Met
            435                 440                 445
Gly Asp Glu Leu Phe Val Asp Phe Leu Lys Arg Cys Leu Asp Trp Asp
        450                 455                 460
Pro Glu Thr Arg Met Thr Pro Ala Gln Ala Leu Lys His Lys Trp Leu
465                 470                 475                 480
Arg Arg Arg Leu Pro Asn Pro Arg Asp Gly Leu Glu Ser Met Gly
                485                 490                 495
Gly Leu Ala Asp His Glu Val Cys Phe Ile Ile Phe
            500                 505
```

(2) INFORMATION FOR SEQ ID NO: 4:

(i) SEQUENCE CHARACTERISTICS:
        (A) LENGTH: 539 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 757823

(xi) SEQUENCE DESCRIPTION: SEQ ID NO: 4:

```
Met His His His Ser Ser Pro Ser Ser Ser Glu Val Arg Ala Met
 1               5                  10                  15

Gln Ala Arg Ile Pro Asn His Phe Arg Glu Pro Ala Ser Gly Pro Leu
            20                  25                  30

Arg Lys Leu Ser Val Asp Leu Ile Lys Thr Tyr Lys His Ile Asn Glu
        35                  40                  45

Val Tyr Tyr Ala Lys Lys Lys Arg Arg Ala Gln Gln Thr Gln Gly Asp
    50                  55                  60

Asp Asp Ser Ser Asn Lys Lys Glu Arg Lys Leu Tyr Asn Asp Gly Tyr
65                  70                  75                  80

Asp Asp Asp Asn His Asp Tyr Ile Ile Lys Asn Gly Glu Lys Phe Leu
                85                  90                  95

Asp Arg Tyr Glu Ile Asp Ser Leu Ile Gly Lys Gly Ser Phe Gly Gln
            100                 105                 110

Val Val Lys Ala Tyr Asp His Glu Glu Gln Cys His Val Ala Ile Lys
        115                 120                 125

Ile Ile Lys Asn Lys Lys Pro Phe Leu Asn Gln Ala Gln Ile Glu Val
130                 135                 140

Lys Leu Leu Glu Met Met Asn Arg Ala Asp Ala Glu Asn Lys Tyr Tyr
145                 150                 155                 160

Ile Val Lys Leu Lys Arg His Phe Met Trp Arg Asn His Leu Cys Leu
                165                 170                 175

Val Phe Glu Leu Leu Ser Tyr Asn Leu Tyr Asp Leu Leu Arg Asn Thr
            180                 185                 190

Asn Phe Arg Gly Val Ser Leu Asn Leu Thr Arg Lys Phe Ala Gln Gln
        195                 200                 205

Leu Cys Thr Ala Leu Leu Phe Leu Ser Thr Pro Glu Leu Asn Ile Ile
    210                 215                 220

His Cys Asp Leu Lys Pro Glu Asn Ile Leu Leu Cys Asn Pro Lys Arg
225                 230                 235                 240

Ser Ala Ile Lys Ile Val Asp Phe Gly Ser Ser Cys Gln Leu Gly Gln
                245                 250                 255

Arg Ile Tyr His Tyr Ile Gln Ser Arg Phe Tyr Arg Ser Pro Glu Val
            260                 265                 270

Leu Leu Gly Ile Gln Tyr Asp Leu Ala Ile Asp Met Trp Ser Leu Gly
        275                 280                 285

Cys Ile Leu Val Glu Met His Thr Gly Glu Pro Leu Phe Ser Gly Cys
    290                 295                 300

Asn Glu Val Asp Gln Met Asn Lys Ile Val Glu Val Leu Gly Met Pro
305                 310                 315                 320

Pro Lys Tyr Leu Leu Asp Gln Ala His Lys Thr Arg Lys Phe Phe Asp
                325                 330                 335
```

-continued

```
Lys Ile Val Ala Asp Gly Ser Tyr Val Leu Lys Lys Asn Gln Asn Gly
                340                 345                 350

Arg Lys Tyr Lys Pro Pro Gly Ser Arg Lys Leu His Asp Ile Leu Gly
            355                 360                 365

Val Glu Thr Gly Gly Pro Gly Gly Arg Arg Leu Asp Glu Pro Gly His
        370                 375                 380

Ser Val Ser Asp Tyr Leu Lys Phe Lys Asp Leu Ile Leu Arg Met Leu
385                 390                 395                 400

Asp Phe Asp Pro Lys Thr Arg Val Thr Pro Tyr Tyr Ala Leu Gln His
                405                 410                 415

Asn Phe Phe Lys Arg Thr Ala Asp Glu Ala Thr Asn Thr Ser Gly Ala
                420                 425                 430

Gly Ala Thr Ala Asn Ala Gly Ala Gly Ser Gly Ser Ser Gly Ala
            435                 440                 445

Gly Gly Ser Ser Gly Gly Val Gly Gly Leu Gly Ala Ser Asn
        450                 455                 460

Ser Ser Ser Gly Ala Val Ser Ser Ser Ala Ala Ala Pro Thr Ala
465                 470                 475                 480

Ala Thr Ala Ala Ala Thr Ala Ala Gly Ser Ser Gly Ser Gly Ser Ser
                485                 490                 495

Val Gly Gly Gly Ser Ser Ala Ala Gln Gln Gln Gln Ala Met Pro Leu
            500                 505                 510

Pro Leu Pro Leu Pro Leu Pro Leu Pro Pro Leu Ala Gly Pro Gly Gly
            515                 520                 525

Ala Ser Asp Gly Gln Cys His Asp Asp Arg Arg
530                 535

(2) INFORMATION FOR SEQ ID NO: 5:

(i) SEQUENCE CHARACTERISTICS:
        (A) LENGTH: 240 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1669685

(xi) SEQUENCE DESCRIPTION: SEQ ID NO: 5:

Pro Tyr Asp Val Ala Ile Asp Met Trp Ser Leu Gly Cys Ile Thr Ala
1                   5                   10                  15

Glu Leu Tyr Thr Gly Tyr Pro Leu Phe Pro Gly Glu Asn Glu Val Glu
                20                  25                  30

Gln Leu Ala Cys Ile Met Glu Val Leu Gly Leu Pro Pro Ala Gly Phe
            35                  40                  45

Ile Gln Thr Ala Ser Arg Arg Gln Thr Phe Phe Asp Ser Lys Gly Phe
    50                  55                  60

Pro Lys Asn Ile Thr Asn Asn Arg Gly Lys Lys Arg Tyr Pro Asp Ser
65                  70                  75                  80

Lys Asp Leu Thr Met Val Leu Lys Thr Tyr Asp Thr Ser Phe Leu Asp
                85                  90                  95

Phe Leu Arg Arg Cys Leu Val Trp Glu Pro Ser Leu Arg Met Thr Pro
                100                 105                 110

Asp Gln Ala Leu Lys His Ala Trp Ile His Gln Ser Arg Asn Leu Lys
            115                 120                 125

Pro Gln Pro Arg Pro Gln Thr Leu Arg Lys Ser Asn Ser Phe Phe Pro
```

-continued

```
            130                 135                 140
Ser Glu Thr Arg Lys Asp Lys Val Gln Gly Cys His His Ser Ser Arg
145                 150                 155                 160

Lys Asp Glu Ile Thr Lys Glu Thr Thr Glu Lys Thr Lys Asp Ser Pro
                165                 170                 175

Thr Lys His Val Gln His Ser Gly Asp Gln Gln Asp Cys Leu Gln His
            180                 185                 190

Gly Ala Asp Thr Val Gln Leu Pro Gln Leu Val Asp Ala Pro Lys Lys
            195                 200                 205

Ser Glu Ala Ala Val Gly Ala Glu Val Ser Met Thr Ser Pro Gly Gln
        210                 215                 220

Ser Lys Asn Phe Ser Leu Lys Asn Thr Asn Val Leu Pro Pro Ile Val
225                 230                 235                 240
```